United States Patent
Stensrud

(10) Patent No.: US 9,463,448 B2
(45) Date of Patent: Oct. 11, 2016

(54) DIALLYL ETHERS OF ANHYDROHEXITOLS AND PROCESSES FOR MAKING THE SAME

(71) Applicant: ARCHER DANIELS MIDLAND COMPANY, Decatur, IL (US)

(72) Inventor: Kenneth Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 42 days.

(21) Appl. No.: 14/401,138

(22) PCT Filed: Apr. 18, 2013

(86) PCT No.: PCT/US2013/037168
§ 371 (c)(1),
(2) Date: Nov. 14, 2014

(87) PCT Pub. No.: WO2013/188004
PCT Pub. Date: Dec. 19, 2013

(65) Prior Publication Data
US 2015/0141671 A1    May 21, 2015

Related U.S. Application Data

(60) Provisional application No. 61/658,118, filed on Jun. 11, 2012.

(51) Int. Cl.
C07D 493/04    (2006.01)
B01J 31/02    (2006.01)
G06F 1/16    (2006.01)

(52) U.S. Cl.
CPC .............. B01J 31/02 (2013.01); G06F 1/1632 (2013.01)

(58) Field of Classification Search
CPC .................................................... C07D 493/04
See application file for complete search history.

(56) References Cited

FOREIGN PATENT DOCUMENTS

JP    2011213716 A    * 10/2011

OTHER PUBLICATIONS

Abele, B.C., et al. "Synthesis of Carbohydrate-Segmented Polydimethylsiloxanes by Hydrosilylation." Journal of Polymer Science, Part A: Polymer Chemistry. (2005), vol. 43(17), pp. 3814-3822.*
Bodner Research Web. "The Chemistry of Halogens." (c) Apr. 2009. Available from: <http://web.archive.org/web/20090414155348/http://chemed.chem.purdue.edu/genchem/topicreview/bp/ch10/group7.php >.*

* cited by examiner

Primary Examiner — Noble Jarrell
Assistant Examiner — John S Kenyon
(74) Attorney, Agent, or Firm — William B. Miller

(57) ABSTRACT

The invention concerns diallylisoidide in a first aspect, and in a related aspect concerns an improved method for making the diallyl ether derivatives of anhydrohexitols generally, whether isosorbide, isomannide, isoidide or a mixture of two or all three of these, whereby these derivatives may be produced efficiently up to quantitative yields.

6 Claims, No Drawings

DIALLYL ETHERS OF ANHYDROHEXITOLS AND PROCESSES FOR MAKING THE SAME

This application is a 35 U.S.C. §371 national phase entry of International Application No. PCT/US2013/037168, filed Apr. 18, 2013, which claims priority from U.S. Provisional Patent Application 61/658,118, filed Jun. 11, 2012.

The present application is in the field of art relating to cyclic bifunctional materials useful as monomers in polymer synthesis and as intermediates generally, and to the methods by which such materials are made.

Terephthalic acid (benzene-1,4-dicarboxylic acid) is a cyclic bifunctional carboxylic acid monomer which finds widespread commercial application as a primary precursor of polyethylene terephthalate (PET), a thermoplastic resin with widespread use in textiles and containers for food, beverages, and other liquids. Terephthalic acid is polymerized, usually with ethylene glycol monomers in an equimolar ratio with terephthalic acid, to yield the polycondensate PET. Terephthalic acid can also be copolymerized with other diacid monomers or esters thereof to obtain polymers with specific desired properties.

Terephthalic acid is commonly produced by oxidation of p-xylene originating from non-renewable petroleum derivatives. However, such petroleum-derived materials are frequently expensive to produce and use because of fluctuations in the pricing and availability of petroleum, and are increasingly likely to remain so as petroleum reserves are reduced and new supplies prove more costly and difficult to secure. Further, PET polymers have raised concerns for their potential to disrupt human endocrine activity, as it has been suggested that PET polymers may release yield endocrine disrupters under commonly used conditions. In addition, PET may under certain conditions break down to yield acetaldehyde, causing the development of off-taste in bottled water. Detectable levels of antimony catalyst are present both inside PET polymers and on the surface, and can migrate into food and beverages in contact with PET, especially fruit juices in PET bottles.

In view of the dependence of conventional PET polymers on increasingly scarce and costly petroleum resources and further in view of the additional concerns surrounding PET polymers just described, renewable source-based alternatives have been earnestly sought. The most abundant type of biobased or renewable source alternative feedstock for producing such materials, namely carbohydrates, are however generally unsuited to current high temperature industrial processes. Compared to petroleum-based, hydrophobic aliphatic or aromatic feedstocks with a low degree of functionalization, carbohydrates such as polysaccharides are complex, overfunctionalized hydrophilic materials.

Consequently, researchers have sought to produce biobased materials that derive from carbohydrates but which are less highly functionalized, including more stable bifunctional materials more or less analogous to terephthalic acid, such as 2,5-furandicarboxylic acid (FDCA), levulinic acid and isosorbide.

Recently, in Wu et al., "Isohexide Derivatives from Renewable Resources as Chiral Building Blocks", ChemSusChem, vol. 4, pp. 599-603 (2011), several C2/C5 carbon-extended bifunctional derivatives were synthesized from isomannide to provide greater reactivity in common melt polycondensation conditions for forming polyester polymers using the isohexicles (or derivatives based thereon). The initial strategy was to make the dinitrile by a nucleophilic substitution of activated hydroxyl groups by cyanide. Unexpectedly for the authors, however, neither the bistosylate nor bismesylate of isomannide showed any reactivity towards cyanide, even though a broad range of reaction conditions were tried. Finally, a successful combination was tried, and the authors were able to obtain the desired dinitrile (in an exo-exo stereochemistry compared to the original endo-endo stereochemistry of the isomannide starting material) through the bistriflate of isomannide, formed by reacting isomannide with trifluorosulfonic anhydride and pyridine in dichloromethane.

Since the diacid was expected to be a possible biobased alternative to terephthalic acid, initial efforts from the dintrile then focused on hydrolysis to the diacid. Various aqueous routes were explored but also proved unsatisfactory; finally it was determined that by making the dinitrile into a dimethyl ester, then purifying the same, the purified dimethyl ester could undergo hydrolysis to provide isoidide dicarboxylic acid. The diacid is described as having been obtained as "a white solid in high isolated yield (84%) and high purity (99.0%)." Other bifunctional derivatives were then also prepared from the isoidide dimethyl ester, in particular, a diol and a diamine.

While the isoidide diacid and other bifunctional derivatives of isoidide were thus eventually successfully made starting from isomannide, the article does also mention the possibility of the like bifunctional derivatives being made starting from the isosorbide and isoidide stereoisomers; but in contemplating this possibility, the authors noted that $S_n2$ reactions on isohexide endo-hydroxyl groups were strongly favored over exo-substitution for steric reasons, and so the authors selected the endo-endo isomannide isomer as a starting material for trying to make the novel bifunctional derivatives in question. The exo-endo isosorbide and exo-exo isoidide derivatives were carried over in the meanwhile for further "investigations."

Similar investigations into the development of biobased, bifunctional materials deriving from carbohydrates were undertaken a number of years prior to Wu et al., in relation to ester as well as ether derivatives. In Gregory et al., "Anhydrides of Polyhydric Alcohols, Part VIII, Some Alkenyl Ethers of 1:4-3:6-Dianhydromannitol and 1:4-3:6-Dianhydrosorbitol", Journal of the Chemical Society (1947), pp. 1405-1407, unsaturated ethers were prepared of isomannide and isosorbide to follow on earlier work to develop diacrylyl and dimethacrylyl esters of these same materials. By treating isomannide and isosorbide with allyl bromide and concentrated sodium hydroxide, the diallyl ethers were prepared in a reported 70% yield. These could then be polymerized. Dimethallyl ethers were also made, with poor yields of the isomannide derivative and better yields of the isosorbide derivative. Polymerization of these materials was reportedly more difficult.

SUMMARY OF THE INVENTION

The present invention in a first aspect concerns the diallyl ether derivative of isoidide ((3R,3aS,6R,6aS)-3,6-bis(allyloxy)hexhydrofuro[3,2-b]furan), referred to hereafter as "diallyl isoidide", which was not included in the allylic derivatives made by Gregory et al.

In a second aspect, the present invention concerns an improved method for making the diallyl ether derivatives of anhydrohexitols such as isosorbide, isomannide and isoidide, whereby much greater yields of these materials can be realized compared to the 70% yields reported by Gregory et al.

DETAILED DESCRIPTION OF PREFERRED EMBODIMENTS

In a first aspect as just mentioned, the present invention concerns diallyl isoidide. Diallyl isoidide is expected to be useful as a monomer for making polymers and as a synthetic intermediate for making a variety of other useful organic compounds. The diallyl ether derivatives of anhydrohexitols generally according to the second aspect, discussed in greater detail later, will have similar utilities.

The starting isoidide material for preparing diallyl isoidide according to the first aspect can be obtained by any known method for making isoidide. According to one embodiment, the isoidide starting material can be prepared by epimerization from isosorbide. In L. W. Wright, J. D. Brandner, *J. Org. Chem.*, 1964, 29 (10), pp 2979-2982, for example, epimerization is induced by means of Ni catalysis, using nickel supported on diatomaceous earth. The reaction is conducted under relatively severe conditions, such as a temperature of 220° C. to 240° C. at a pressure of 150 atmosphere. The reaction reaches a steady state after two hours, with an equilibrium mixture containing isoidide (57%), isosorbide (36%) and isomannide (7%). Comparable results were obtained when starting from isoidide or isomannide. Increasing the pH to 10-11 was found to have an accelerating effect, as well as increasing the temperature and nickel catalyst concentration. A similar disclosure is to be found in U.S. Pat. No. 3,023,223.

In EP 1 647 540, L-iditol is prepared starting from sorbitol. In a first step sorbitol is converted by fermentation into L-sorbose, which is subsequently hydrogenated into a mixture of D-sorbitol and L-iditol. This mixture is then converted into a mixture of L-iditol and L-sorbose. After separation from the L-sorbose, the L-iditol can be converted into isoidide. Thus, sorbitol is converted into isoidide in a four-step reaction, in a yield of about 50%.

A preferred method for preparing isoidide by the epimerization of isosorbide is described in European Patent Application No 12156170.8, "Method of Making Isoidide", filed Feb. 20, 2012, wherein a supported ruthenium catalyst is used at a starting pH of above 7, preferably of from 8 to 10, with the starting pH referring to the pH of the aqueous solution of isosorbide.

The epimerization of isosorbide into isoidide is conducted according to this process under relatively mild conditions, such that an equilibrium production of isoidide can be attained while avoiding mass losses through hydrodeoxygenation and providing a better overall yield compared to the results of Wright and Brandner.

The support can vary widely, including silica, alumina, titanic, zirconia, and carbon. A carbon support is preferred, inter alia since it can be operated at a wider pH range than other supports. As well, a carbon supported ruthenium catalyst was observed to act more favorably in the epimerization of isosorbide, than other supports, e.g., Al2O3. The catalytically active metal preferably consists essentially of ruthenium, and the support preferably consists essentially of carbon. A suitable ruthenium content is described as from 1% to 10% by weight of ruthenium, based on the total weight of the catalyst, preferably being about 5% by weight of the catalyst.

In order to conduct the epimerization, isosorbide is provided in the form of an aqueous solution. The concentration of isosorbide therein may widely vary. However, for the sake of process economics as well as results in terms of yield, it is preferred for the isosorbide concentration to be in a range of from 25% by weight to 75% by weight. More preferably, the isosorbide concentration is 30% to 60% by weight. The optimum concentration is believed to approximately 50% by weight.

The aqueous solution is subjected to an atmosphere comprising hydrogen. The hydrogen pressure can widely vary, for example, from 20 to 200 bars. However, it was found particularly effective to employ a relatively low pressure in the range of from to 55 bars, and preferably about 40 bars.

Calculated on the basis of a water paste comprising 50% of a 5% ruthenium on carbon catalyst, the catalyst concentration in the reactor, calculated as a weight percentage based on the aqueous solution of isosorbide, can range from as low as, e.g., 1% to as high as, e.g. 50%. However, for the sake of process economics as well as results in terms of yield and specificity, it is preferred for a 5% ruthenium catalyst to be employed in a concentration of from 2 to 20%, and more preferably about 4%. It will be understood that these percentages will hold, mutatis mutandis, for other water paste concentrations than 50%, and other catalyst loadings than 5%.

The skilled person will be aware of how to generally conduct the ruthenium catalyzed reaction. Background references in this respect include U.S. Pat. No. 6,177,598 and U.S. Pat. No. 6,570,043.

The ruthenium catalyst as mentioned preferably comprises a carbon support. Different types of carbon support are applicable, e.g. activated carbon or carbon nanotubes. The activated carbon can be, e.g., 50-70% wetted powder. Typically preferred catalysts include commercial ruthenium on carbon catalysts ex BASE or Evonik (Stem Chemicals). A background reference on Ru/C catalysts is Sifontes Herrera et al, J. Chem Technol Biotechnol (2011), "Sugar hydrogenation over a Ru/C catalyst."

The epimerization reaction is conducted preferably at an elevated temperature, i.e. above 20° C., and preferably below 250°. A preferred temperature range is 200° to 240°, most preferably about 220° C. The duration of the reaction will, as the skilled person knows, generally be shorter at higher temperatures. The residence time in the reactor where the isosorbide solution is subjected to hydrogen under the influence of the catalyst, will generally range from 0.1 to 10 hours, preferably 0.25 to 4 hours, and more preferably from 1 to 2 hours.

It is preferred to adjust the pH of the aqueous solution of isosorbide. Although the epimerization may be conducted successfully over a range of pH values, it has been found that unwanted side reactions (leading to a loss of matter as a result of the formation of volatiles) can be reduced considerably by adjusting the pH to a value of 8 to 10.

From the equilibrium mixture, the isoidide starting material can be recovered by separation methods known to the skilled person, such as by chromatographic techniques, selective crystallization or distillation. The latter can be conducted, e.g. as disclosed by Wright et al. J. Org. Chem., 1964, 29 (10), pp 2979-2982, mentioned above. Other references descriptive of methods for separating an epimerization mixture of isosorbide, isomannide and isoidide include commonly-assigned U.S. Pat. No. 7,439,352 and U.S. Pat. No. 6,849,748 to Moore et al, both of which are hereby incorporated herein by reference, as well as U.S. Pat. No. 6,670,033 to Hubbard et al., U.S. Pat. No. 4,564,692 to Feldman et al., U.S. Pat. No. 7,122,661 to Fleche at al, and U.S. Pat. No. 8,008,477 to Fuertes.

Once the isoidide starting material has thus been obtained, the diallyl isoidide can be made quantitatively, as illustrated by the example below, by a novel process for making the diallyl ether derivatives of any one or more of isosorbide, isomannide and isoidide according to a second, more general aspect of the invention.

According to the previously mentioned process of Gregory et al. (1947), dianhydrosorbitol or dianhydromannitol was suspended in allyl bromide with stirring at 70 degrees Celsius. Concentrated sodium hydroxide solution was then added slowly during the period of 1 to 25 hours, with continued stirring on completing the addition of sodium hydroxide for 1 to 75 hours. Water was then added, and any unsaturated volatile compounds present were removed by steam distillation. The mixture was then extracted with ether, the organic extract was water-washed and the washed organic extract then was dried with magnesium sulfate. After removal of the ether from the organic phase remaining, a light brown, mobile liquid remained which was twice distilled under reduced pressure in a carbon dioxide atmosphere.

According to the present inventive process, in contrast, in one embodiment a dianhydrohexitol or mixture of dianhydrohexitols is reacted with a Brønsted base whose conjugate acid has an acid dissociation constant $pk_a$ greater than 16. Preferably, the Brønsted base has a $pk_a$ of about 18 or greater. In one embodiment, the Brønsted base is potassium t-butoxide; butanol, the conjugate acid of t-butoxide, has a $pK_a$ of about 18.

Using sodium hydroxide, as taught by Gregory et al. in relation to making the allyl ethers of dianhyosorbitol and dianhydromannitol, would in the context of making the diallylisoidide result in a general equilibrium between reactants and products as the alcohol functionalities of isoidide and water generated in the product have approximately equivalent acid dissociation constants of about 16:

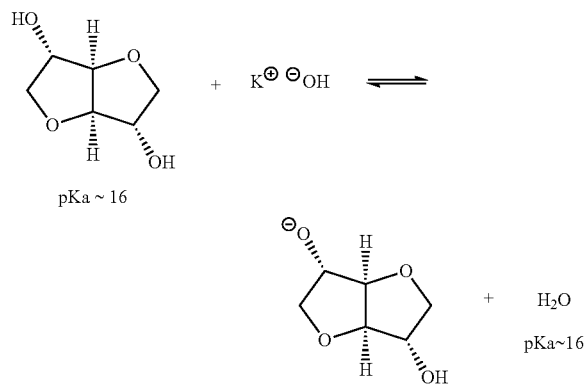

By using a Brønsted base whose conjugate acid has an acid dissociation constant $pK_a$ greater than 16, for example, a Brønsted base such as potassium t-butoxide, formation of the nucleophilic isoidide anion intermediate is thermodynamically favored:

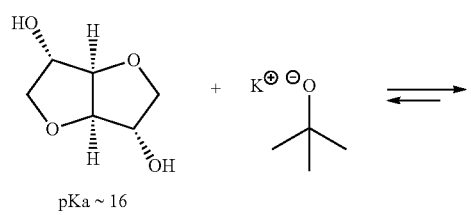

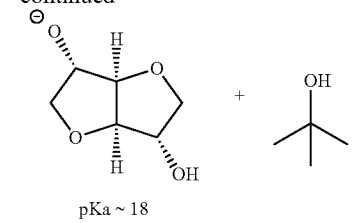

Moreover, while the hydroxide ion is a reasonably potent nucleophile and can be expected to produce allyl alcohol as a secondary product, t-butoxide is sterically hindered from appreciably reacting with allyl bromide when the same is subsequently added to the isoidide conjugate base(s)/residual potassium butoxide mixture at the temperatures contemplated by the inventive process and made possible by the selection and use of Brønsted bases such as potassium butoxide whose conjugate acids have higher acid dissociation constants.

In a preferred embodiment, the isohexide stereoisomer or stereoisomers and the Brønsted base are reacted in a non-aqueous solvent system, in the substantial absence of water. In this regard, while Gregory et al. proposed utilizing aqueous sodium hydroxide, in the presence of water the hydroxide would be fully solvated or hydrogen bonded, and consequently less effective in deprotonating isoidide to its anion intermediate. Heating would be helpful to Gregory et al. in this circumstance, but as noted above, higher temperatures would be expected to contribute to yield losses to allyl alcohol and other side products. Additionally, allyl bromide is insoluble in water, so that a difficult two-phase reaction system would ensue on addition of the base. A preferred nonaqueous solvent is dimethylformamide.

As an additional preferred feature, owing to the ready formation of the conjugate base(s) of the isohexide/dianhydrohexitol in the initial combination of the Brønsted base(s) with the dianhydrohexitol(s), the overall process can be carried out at lower temperatures. For example, in one embodiment, the process is conducted at a reaction temperature of about 25 degrees Celsius or less. In another embodiment, the process is conducted at a reaction temperature of about 20 degrees Celsius or less. While t-butoxide as noted above is less likely to react with the allyl bromide compared to Gregory et al's sodium hydroxide at any given temperature, at these preferred lower temperatures the activation barrier to reaction of t-butoxide with allyl bromide will be correspondingly less likely to be surmounted.

In other embodiments, allyl bromide is added to the conjugate base(s) of the isohexide stereoisomer or stereoisomers gradually over time to reduce the availability of this reagent to react with residual Brønsted base, a less-favored (but still possible) side reaction at these reaction temperatures. In certain embodiments, for example, not more than about 13.3% percent allyl bromide is added per minute.

The present invention is further illustrated by the following examples:

Example 1

A 50 mL round-bottomed flask was charged with 2 grams of isoidide and 3.38 grams of potassium t-butoxide. The homogeneous mixture was chilled to about 0 degrees Celsius in a saline/ice bath, the flask was purged with argon, and 25 mL of anhydrous dimethylformamide was added dropwise with continuous magnetic stirring for 15 minutes. After this time while maintaining a 0 degrees Celsius bath, 2.38 mL of allyl bromide was added dropwise over a period of 15 minutes. As the addition proceeded, the flask contents were observed to change from a clear, colorless solution to having a light yellowish hue. After complete addition of the allyl bromide, the saline/ice bath was removed and the reaction was continued overnight. An aliquot was removed after this time, diluted with methylene chloride, and injected into a GC/MS (APCI), which indicated full conversion had been attained. The flask contents were transferred to a 250 mL separator/funnel, diluted with 50 mL of methylene chloride and 50 mL of water, shaken vigorously, and then the aqueous phase was removed. The organic phase was then washed with three successive 50 mL volumes of water, removing the aqueous phase after each addition/agitation. The remaining organic phase was dried with anhydrous magnesium sulfate, then concentrated in vacuo, producing a 3.10 g of a loose, yellow oil (100%). Analysis of the oil produced the following results, and indicated a quantitative yield of diallyl isoidide: 1H NMR (CDCl3, 400 MHz), δ (ppm) 5.89-5.82 (m, 2H), 5.28-5.26 (dd, J=7.2 Hz, J=2.0 Hz, 2H), 5.24-5.22 (dd, J=7.4 Hz, J=1.6 Hz, 2H), 4.59 (s, 2H), 4.03-3.98 (m, 2H), 3.86-3.78 (m, 4H), 2.93 (s, 2H), 2.85 (s, 2H). $^{13}$C NMR (CDCl3, 100 MHz) δ (ppm) 134.35, 117.67, 85.63, 83.10, 72.47, 70.75. HRMS (GC/TOF, M+H) Calculated for C12H18O4: 227.1283. Found: 227.1294.

The process can be illustrated as follows:

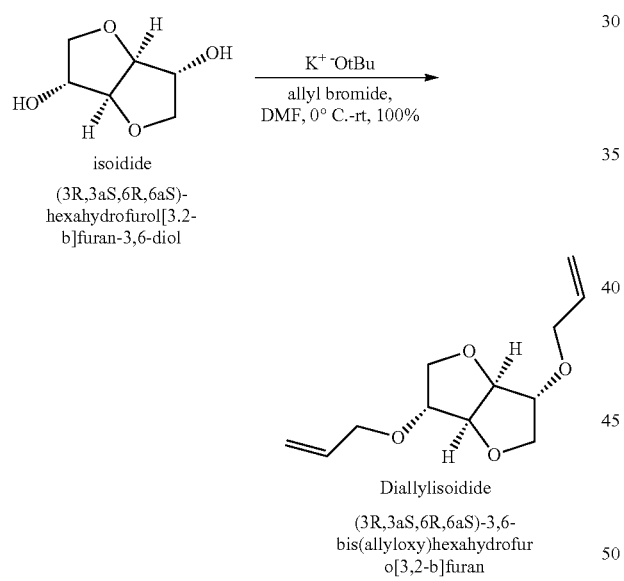

isoidide
(3R,3aS,6R,6aS)-hexahydrofuro[3.2-b]furan-3,6-diol

Diallylisoidide
(3R,3aS,6R,6aS)-3,6-bis(allyloxy)hexahydrofuro[3,2-b]furan

Example 2

Diallylisomannide, (3R,3aR,6R,6aR)-3,6-bis(allyloxy)hexahydrofuro[3,2-b]furan, was synthesized as follows: A dry, 2-neck, 100 mL boiling flask was charged with 2.00 g of isomannide (13.7 mmol), 3.38 g of potassium t-butoxide (30.1 mmol) and 25 mL of dimethylformamide. A rubber septum was placed over one of the necks, while an argon line was outfitted onto the other. The heterogeneous mixture was purged with argon, and concomitantly cooled to about 0 degrees Celsius in a brine/ice bath. While vigorously stirring, 2.38 mL, (27.4 mmol) of allyl bromide was injected through the septum over 15 minutes. Once complete addition had occurred, the ice bath was removed, allowing the reaction mixture to warm to room temperature overnight. After this time, a light yellow solution with profuse white precipitate was observed. The solution was transferred to a 250 mL round bottomed flask, and diluted with 100 mL of methylene chloride and 100 mL of water. The water addition quickly dissolved the solids and resultant biphasic mixture was stirred vigorously. The bottom organic phase was removed and diluted with 100 mL more of water. After stirring, the organic phase was again removed, dried with anhydrous magnesium sulfate and concentrated in vacuo, furnishing a loose, light yellow oil, 2.92 g (94% of theoretical yield). Thin layer chromatography (5:1 hexanes/ethyl acetate) indicated only one spot (rf=0.4). 1H NMR (CDCl3, 400 MHz) δ (ppm) 5.90-5.88 (m, 2H), 5.29 (d, J=4.2 Hz, 1H), 5.27 (d, J=6.8 Hz, 2H), 5.25 (d, J=3.8 Hz, 1H), 5.16 (d, J=7.8 Hz, 2H), 4.50 (d, J=3.0 Hz, 2H), 4.13 (d, J=3.3 Hz, 1H), 4.11 (d, J=3.8 Hz, 1H), 4.04-4.00 (m, 5H), 3.68 (s, 1H). 13C NMR (CDCl3, 125 MHz) δ (ppm) 134.74, 117.95, 80.63, 79.90, 71.91, 71.26.

The process can be illustrated as follows:

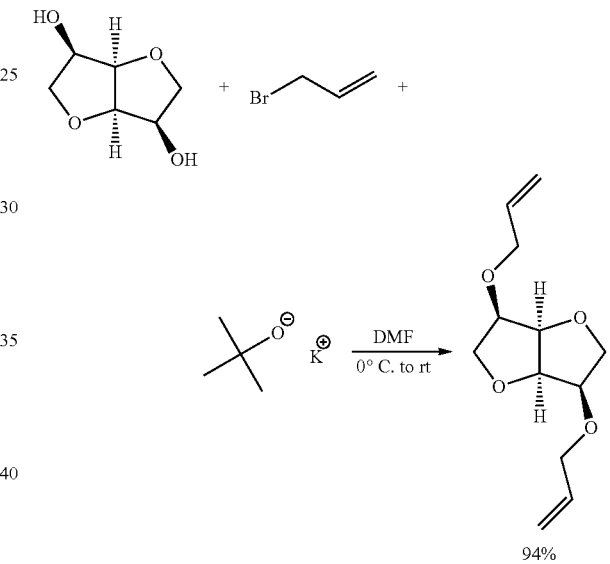

The invention claimed is:

1. A process for forming diallylisoidide from isosorbide, comprising:
    subjecting isosorbide to catalyzed epimerization to form a mixture of isosorbide, isomannide and isoidide;
    separating out an isoidide product from the mixture;
    reacting the isoidide product with a Brønsted base whose conjugate acid has an acid dissociation constant pKa greater than 16, to form a conjugate base of isoidide; and
    reacting the conjugate base of isoidide with allyl bromide to form diallylisoidide.

2. The process of claim 1, wherein the epimerization step involves subjecting an aqueous solution of isosorbide to epimerization in the presence of hydrogen under the influence of a catalyst comprising ruthenium on a support, at a starting pH of above 7.

3. The process of claim 1, wherein the Brønsted base is potassium t-butoxide.

4. The process of any one of claims 1, 2 or 3, wherein the isoidide product and Brønsted base are reacted in a non-aqueous solvent system, in the substantial absence of water.

5. The process of claim 4, wherein allyl bromide is added to the conjugate base of isoidide gradually over time.

6. The process of claim 5, wherein the reaction temperature is 25 degrees Celsius or less.

* * * * *